(12) United States Patent
Gao

(10) Patent No.: US 8,113,095 B2
(45) Date of Patent: Feb. 14, 2012

(54) TORQUE MEASURING MECHANISM USING CAM ENGAGEMENT

(75) Inventor: Hua Gao, Fox Point, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 445 days.

(21) Appl. No.: 12/378,241

(22) Filed: Feb. 12, 2009

(65) Prior Publication Data

US 2010/0204703 A1 Aug. 12, 2010

(51) Int. Cl.
*B25B 23/157* (2006.01)

(52) U.S. Cl. ........................ 81/474; 73/862.21

(58) Field of Classification Search ............ 81/473–476, 81/58; 464/36; 192/56.57, 56.62; 73/862.08, 73/862.191, 862.21, 862.23
See application file for complete search history.

(56) References Cited

U.S. PATENT DOCUMENTS

| | | | |
|---|---|---|---|
| 1,566,553 A | 12/1925 | Maisch | |
| 1,860,871 A | 5/1932 | Pouliot | |
| 2,332,971 A | 10/1943 | Johnson | |
| 2,802,354 A | 8/1957 | Bohnhoff et al. | |
| 3,168,944 A | 2/1965 | Livermont | |
| 3,277,670 A | 10/1966 | Bent | |
| 3,277,671 A | 10/1966 | Winstone et al. | |
| 3,305,058 A | 2/1967 | Orwin et al. | |
| 3,613,751 A | 10/1971 | Juhasz | |
| 3,653,226 A | 4/1972 | Westbury | |
| 3,702,546 A | 11/1972 | Schnepel | |
| 3,942,337 A | 3/1976 | Leonard et al. | |
| 4,041,729 A | 8/1977 | Bilz | |
| 4,668,206 A | 5/1987 | Fukumoto | |
| 4,712,456 A | 12/1987 | Yuan | |
| 4,759,225 A | 7/1988 | Reynertson et al. | |
| 5,035,311 A | 7/1991 | Girguis | |
| 5,054,588 A | 10/1991 | Thorp et al. | |
| 5,156,244 A | 10/1992 | Pyles et al. | |
| 5,356,350 A | 10/1994 | Schreiber | |
| 5,383,818 A | 1/1995 | Lessat-Kaupat et al. | |
| 5,505,676 A | 4/1996 | Bookshar | |
| 6,132,435 A | 10/2000 | Young | |
| 6,439,086 B1 * | 8/2002 | Bahr | ............ 81/467 |
| 6,640,674 B1 | 11/2003 | Rinner et al. | |
| 6,834,864 B2 | 12/2004 | Girardeau | |
| 6,990,877 B1 | 1/2006 | Wu | |
| 6,997,084 B1 | 2/2006 | Gao et al. | |

* cited by examiner

*Primary Examiner* — Debra S Meislin
(74) *Attorney, Agent, or Firm* — Ryan Kromholz & Manion, S.C.

(57) ABSTRACT

A device for delivering a predetermined amount of torque to a tool. The device has a handle and a cam assembly located within the handle. The cam assembly has a cam member integrally formed with a drive shaft. An adjustment ring is capable of rotating the cam assembly to different positions related to different levels of torque. A plunger will be biased against an exterior surface of the cam member to provide the different levels of torque delivery.

20 Claims, 5 Drawing Sheets

US 8,113,095 B2

TORQUE MEASURING MECHANISM USING CAM ENGAGEMENT

BACKGROUND OF THE INVENTION

The present invention relates to handheld tools and devices and, more particularly, to handheld tools and devices that have torque measuring mechanisms included with the tools.

Screwdrivers, wrenches and the like have been developed to allow for varying degrees of torque to be delivered upon an object. These devices allow for different tensions or torques to be built into a torque-limiting device. Generally, such drivers use torsion springs or torsion beams in connection with a tensioning or biasing device to adjust or vary the amount of torque being delivered to an object. In certain devices and drivers, such as devices used in the medical field, these devices must be able to exert a large amount of force, while retaining a high level of precision. The large amount of force delivered by these devices tends to put a large amount of stress on the springs, which diminishes the strength of the spring, thereby reducing the precision of the spring.

Likewise, drivers and the like may be required to deliver differing amounts of torque at different times. That is, the same driver may be required to deliver a first amount of torque for a first procedure or step and a second amount of torque for a second procedure or step. These different steps still require precision. It is essential that one may be able to change from one setting to another accurately without losing precision. That is, the biasing means used in the devices should remain accurate even after several adjustments between varying tension settings. Previous designs that use springs or beams, as discussed above, tend to wear after some use, thereby reducing the accuracy of the device.

SUMMARY OF THE INVENTION

The present invention provides a torque measuring mechanism for a tool driver that is based upon engagement of a cam and biasing means located within the tool to deliver a preset amount of torque. The mechanism generally comprises a cam connected to a drive shaft located within a handle. A support sleeve positioned over the drive shaft is fixed to the handle, which in turn is connected to an adjustment ring that allows for various levels of torque to be fixed for the tool.

The cam interacts with a rolling member that is positioned between the cam and a plunger, with the interaction of these components providing the ability to limit the torque within the device. The rotation of the cam determines the amount of torque being delivered by the driver. The interaction allows the device to potentially have more than one preset level of torque being delivered by the tool.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
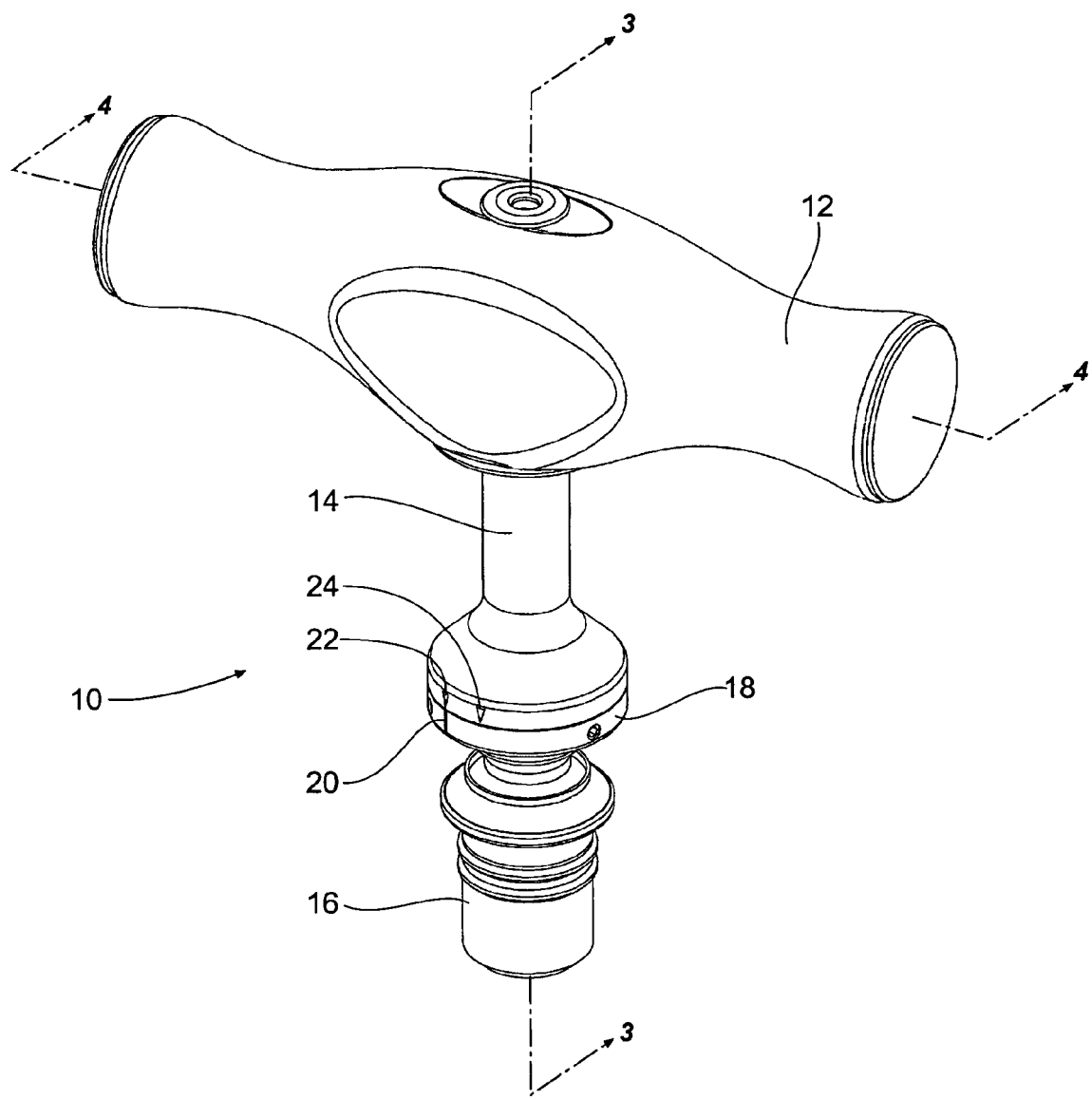
FIG. 1 is a perspective view of a torque measuring tool according to the present invention.

FIG. 1 provides a perspective view of a torque measuring driver 10 in accordance with the present invention. The driver 10 generally comprises a handle 12, a support sleeve or support section 14, and an adapter 16 that will allow attachment to a tool, such as a screwdriver, drill bit, wrench, or another similar device or tool (not shown). The driver 10 further comprises an adjustment ring 18 having an indicator 20 that will correspond to various torque measurements, such as markings 22 and 24 located on the external surface of the support section 14. The adjustment ring 18 allows the driver 10 to provide more than one level of preset torque for the user.

Figure 2:
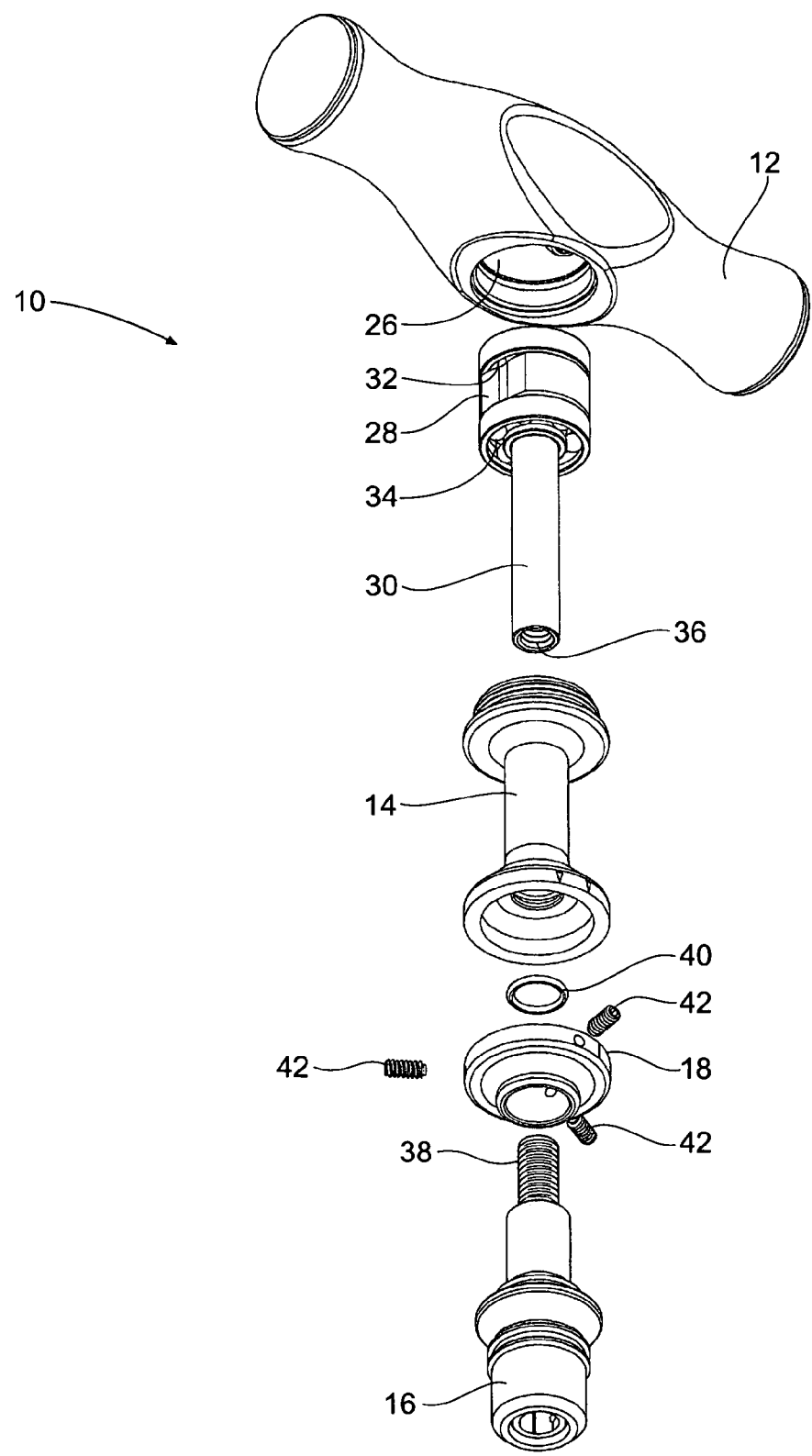
FIG. 2 is an exploded perspective view of the tool shown in FIG. 1.

FIG. 2 is an exploded view of the driver 10. The handle 12 further comprises a housing 26 that will allow a cam member 28 to be situated within the housing 26. The cam member 28 is supported by a drive shaft 30, which together form a cam assembly, preferably with the drive shaft 30 and the cam member 28 formed as a single piece. The cam member 28 has a pair of ball bearings 32 and 34 located vertically above and below the cam member 28 to provide horizontal support and balance for the cam member 28. The drive shaft 30 is seated within the support section 14, and is arranged to pass through the support section 14 to interact with the adapter 16. The drive shaft 30 has an internally threaded end 36 that is situated to be securely mated with an externally threaded portion 38 of the adapter 16. An O-ring 40 is positioned over the threaded portion 38 to further provide a proper fit between the adapter 16 and the drive shaft 30.

Still referring to FIG. 2, the adjustment ring 18 is matingly situated over the outside of the adapter 16 and further held in place with a plurality of set screws 42 that intersect corresponding threaded pathways 44 located in the adjustment ring 18. The adjustment ring 18 is designed to move or rotate the drive shaft 30 and the cam member 28.

Figure 3:
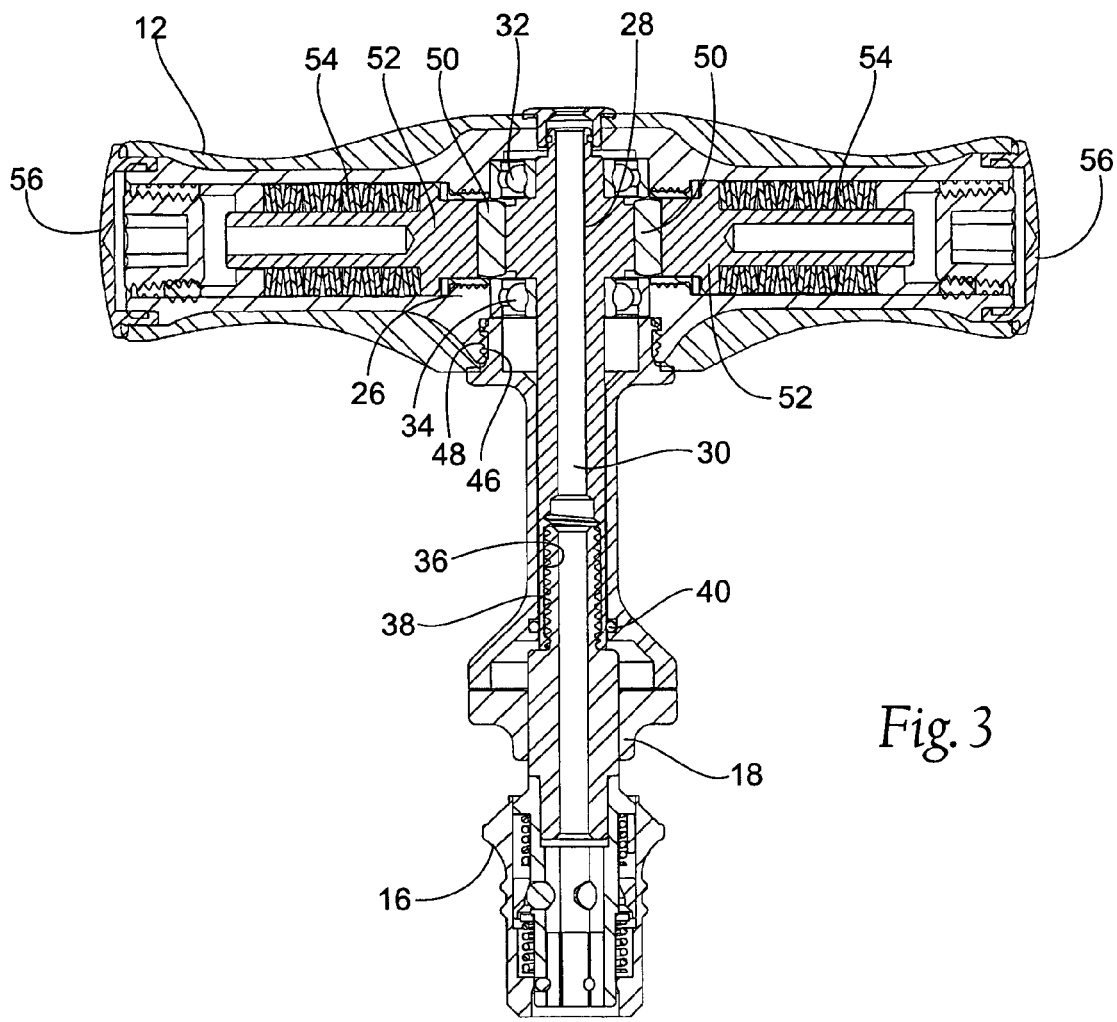
FIG. 3 is a cross-sectional view of the tool of FIG. 1 taken along the line 3-3 of FIG. 1.

FIG. 3 provides a cross-sectional of driver 10 taken along line 3-3 of FIG. 1. As previously noted, the adapter 16 is secured to the drive shaft 30 by way of the threaded surface 36 of the drive shaft 30 being mated with the threaded portion 38 of the adapter 16. The support section 14 fits over the drive shaft 30 and will be secured to the handle 12, preferably with a threaded surface 46 of the support section 14 being threaded onto a threaded surface 48 of the handle 12. The cam member 28 is located within the handle 12, preferably centrally located within the housing 26 formed by the handle 12. The bearings 32 and 34 are aligned above and below the cam member 32 to provide horizontal alignment for the cam member 28. The cam member 28 is arranged to interact with a pair of rolling members 50, which are positioned between the cam member 28 and a respective plunger 52. Alternatively, the plungers 52 could be designed as a single, integral structure with the rolling members 50. The plungers 52 are biased inwardly towards the cam member 28 by way of springs 54 that are held in place within the handle 12 by way of caps 56 located at opposing ends of the handle 12. The caps 56 are preferably threaded onto the handle 12, but could be attached to the handle by any means, such as bolts, clips, adhesives, or other arrangements that would provide the necessary arrangement and biasing means for the plungers 52 with respect to the cam member 28.

Figure 4:
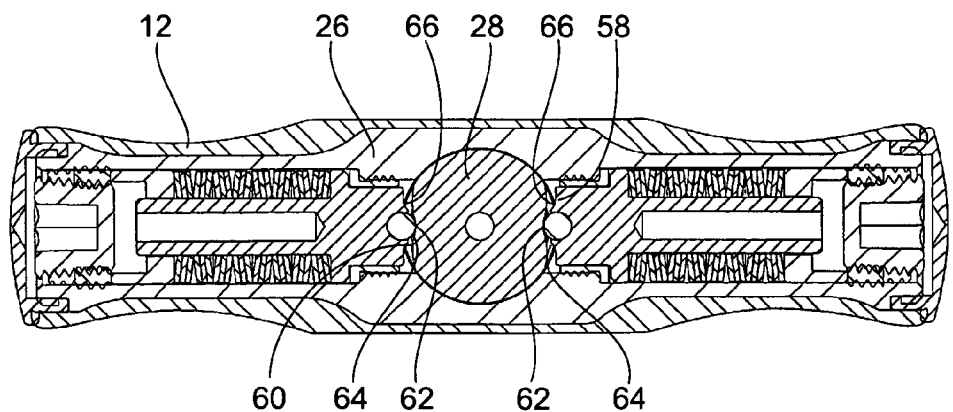
FIG. 4 is a cross-sectional view of the tool of FIG. 1 taken along the line 4-4 of FIG. 1.

FIG. 4 provides an overhead sectional view of the handle 12, taken along line 4-4 of FIG. 1. The cam member 28 is depicted at a first position, a resting or zero position, within the housing 26. Referring back to FIG. 1, the zero or resting position would correspond to when the indicator 20 is aligned with the marking 22. Referring again to FIG. 4, the surface of the cam member 28 comprises a pair of opposing side surfaces 58 and 60. Each of the side surfaces 58, 60 generally comprises a recessed area 62 formed between sections 66 and 64, which are radially outwardly extending from the cam member 28 when compared to the recessed area 62. That is, the recessed areas 62 form indentations on the cam member 28 compared to the sections 66 and 64. The recessed areas 62 provide an area where the rolling members 50 are normally positioned between the cam member 28 and the plungers 52 when the mechanism is arranged at the zero position. The mechanism 10 will be able to deliver a preset of torque at the zero position.

Figure 5:
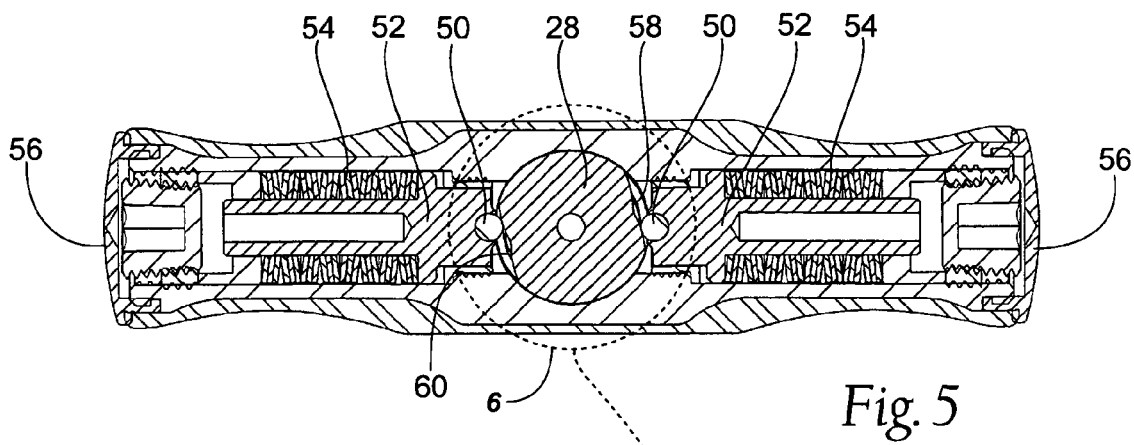
FIG. 5 is a cross-sectional as shown in FIG. 4, with the cam mechanism shown in a second, engaged position.

FIG. 5 provides a second view of the handle 12, with the cam member 28 and the rolling members 50 being at a second position from that shown in FIG. 4, with the second position being referred to as the drive position. The second position would correspond to the indicator 20 aligning with the marking 24 of FIG. 1. Thus, by rotating the adjustment ring 18 from a first position to second position, the drive shaft 30 will move the cam member 28 from the position shown in FIG. 4 to the position shown in FIG. 5.

Figure 6:
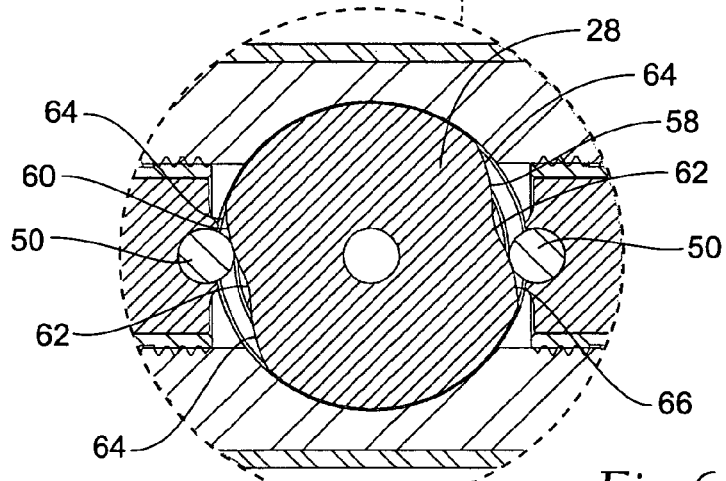
FIG. 6 is an enlarged view of the cam mechanism of FIG. 5 taken along the line 6-6.

FIG. 6 provides a close-up view of the cam member 28 shown in FIG. 5. The cam member 28 has been rotated, wherein the rolling members 50 are shown buttressed against one of the respective sections 66 or 64, thereby providing the desired torque for the driver 10. The interaction between the cam member 28 and the rolling members 50 and the plungers 52 provides the necessary resistant so that the arrangement shown in FIGS. 5 and 6 will set the maximum amount of torque being delivered by the driver 10. Because of the arrangement of the cam assembly and the design of the cam member 28, itself, the driver 10 does not require extra tension or torsion beams or springs to provide the necessary torque delivered by the tool.

Likewise, the interaction of the cam member 28 and the rolling members 50 insures that the maximum amount of torque will be properly delivered without overloading the driver 10. That is, the maximum amount of torque will be delivered with minimal concern that the rolling members 50 will move past the edges of the side surfaces 58, 60. As shown in FIGS. 5 and 6, the maximum amount of torque is delivered when the rolling members 50 are approximately centrally located on the outwardly extending sections 64 or 66, depending on the direction the driver 10 is being used. The rolling member 50 will be biased against the cam member 28, with the arrangement being held securely in place, since the cam assembly (i.e. the cam member 28 and the drive shaft 30) is turned together to achieve this position. That is, the cam assembly is designed as a single, unitary element, thereby minimizing any unnecessary strain or torque between the cam member 28 and the drive shaft, as in prior art designs. Likewise, because of the curvilinear shape of the surfaces 58 and 60, there is not the harsh interaction of a rolling member moving from one slot to another on a cam member as in prior art arrangements, which increases and extends the accuracy of the driver 10. Preferably, the driver 10 will deliver at least two predetermined levels of torque, with the minimum level of torque delivery being when the rolling members 58 and 60 are arranged to interact with recessed area 62 of the cam member 28, while the maximum level of torque delivery will be when cam member 28 is rotated so that the rolling members 58 and 60 are arranged to interact with a respective section 64 or 66, approximately with a central area of the section 64 or 66, as depicted in FIGS. 5 and 6.

Figure 7:
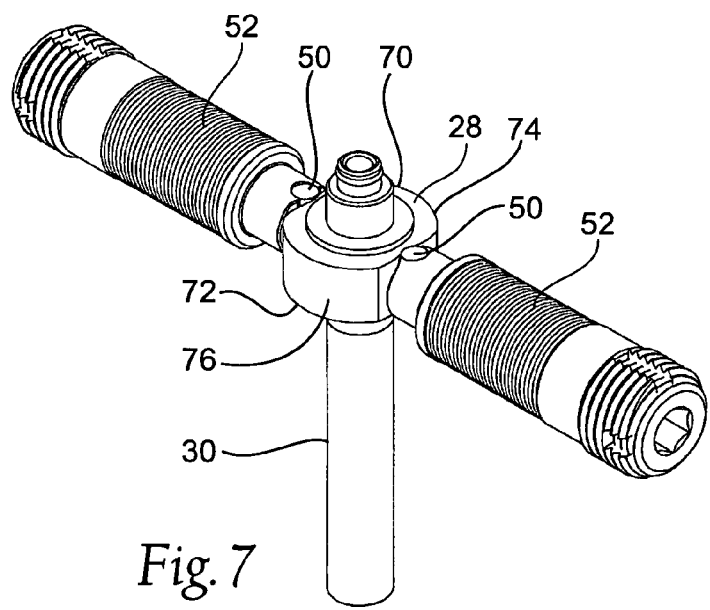
FIG. 7 is a perspective view of a cam mechanism, drive shaft, and plungers and rolling members that are arranged to interact with the cam mechanism.

FIG. 7 provides a perspective view of the cam member 28, the plungers 52, and the drive shaft 30. As previously noted, the drive shaft 30 and the cam member 28 are formed as a single element. This allows the plungers 52 to provide the necessary amount of torque to the cam member 28, without putting unnecessary stress on the drive shaft 30. Since the drive shaft 30 and the cam member 28 are rotated with one another, the cam member 28 will not twist separately from the drive shaft 30, thereby providing an accurate amount of torque delivered by the driver 10. Also, adjustment of the amount of torque delivered by the driver is done by rotating the cam assembly, as opposed to adjusting the tension within or produced by the biasing means (the plungers 52 and the rolling members). Once the biasing means are situated within the housing 26, they are not adjusted to change the amount of torque delivered by the driver 10. Rather, the torque delivery is adjusted by rotating the cam assembly, as described above.

Still referring to FIG. 7, the cam member 28 is described in more detail. The cam member 28 has a top surface 70 and a bottom surface 72, which the bearings 32 and 34 (see FIG. 3) are situated upon, as previously described. The cam member has a front side surface 72 and a rear side surface 74, which preferably form a partial circular arrangement. As previously discussed with respect to FIGS. 5 and 6, the cam member 28 also has the curvilinear side surfaces 58 and 60. The plungers 52 extend laterally away from the side surfaces 58 and 60 and provide the necessary bias needed so that the driver can deliver a predetermined amount of torque. As shown in FIGS. 5 and 6, the cam member 28 is rotated to change the amount of torque delivered, while the plungers 52 are held in a constant position while the cam member 28 is rotated to a different position.

The arrangement is unique when compared to previous drivers and devices that were capable of delivering preset amounts of torque. Previous drivers used torsion beams or torsion springs to provide measured amounts of torque for a driver. The present arrangement removes the need for torsion beams or torsion springs, thereby providing a more straightforward, consistent device for delivering torque. The present invention could also be used for axially aligned drivers. Provided that biasing means were arranged within the driver to interact with cam assembly as described, the driver would fall within the scope of the present invention.

Figure 8:
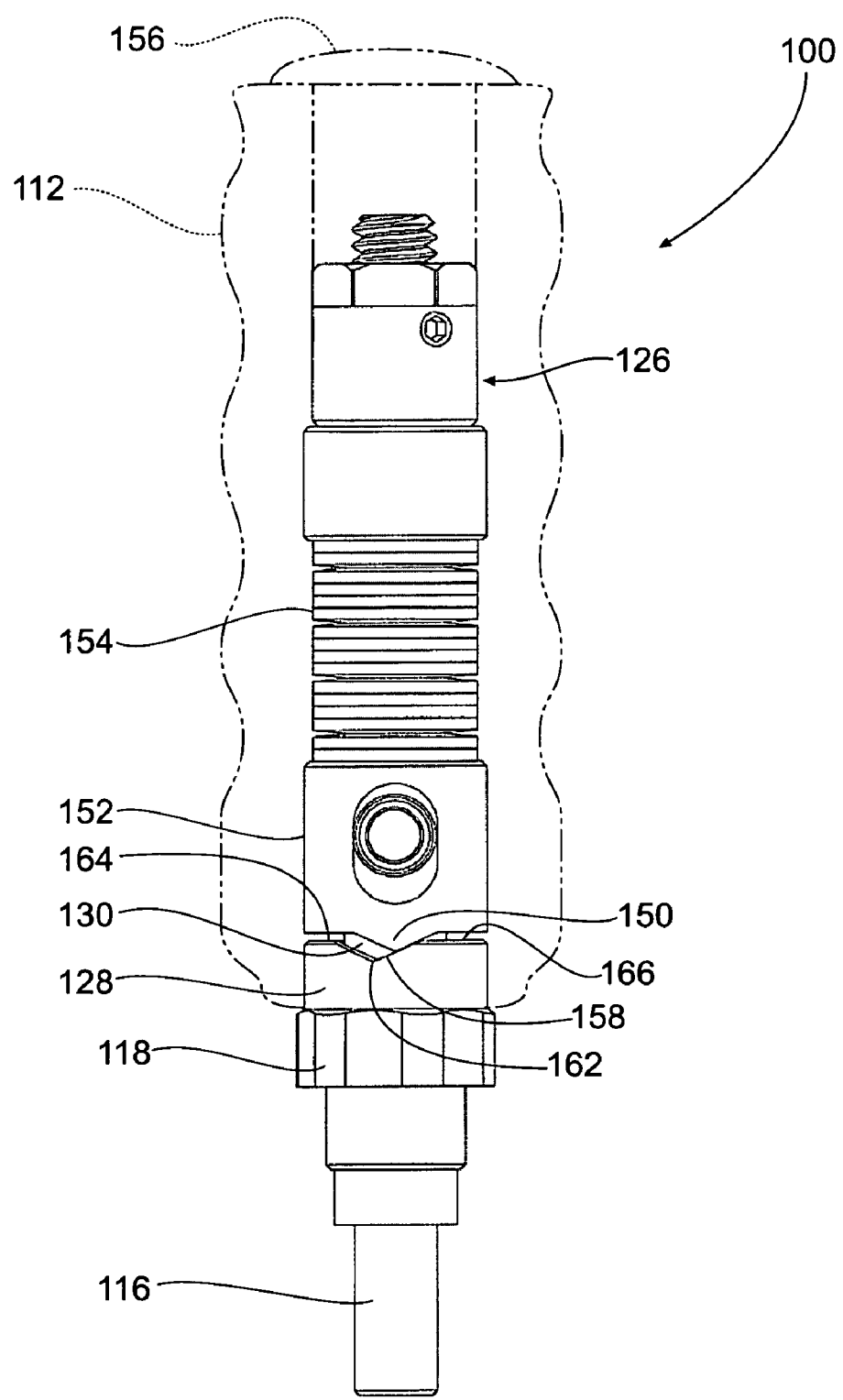
FIG. 8 is a front elevation view of another embodiment of a cam mechanism according to the present invention, with the cam mechanism being used in an axial driver.

For example, FIG. 8 shows an alternate embodiment of a driver 100 that is an axially arranged driver, with the various interacting elements of the driver 100 generally being coaxially aligned with one another. The driver 100 has a handle 112 that provides a housing 126 for various elements of the driver 100. The handle 112 is connected to an adapter 116, similarly to the arrangement described with respect to the driver 10 and the adapter 16 and handle 12. An adjustment ring 118 is connected to a shaft 130, which in turn is connected to a cam member 128. The cam member 128 and the shaft 130 comprise a cam assembly, and are rotated by the adjustment ring 118 to provide various levels of torque delivery, as previously described. As with the previous driver 10, the cam member 128 interacts with biasing means, generally comprises at least one roller member 150 and a plunger 152. As depicted in FIG. 8, the roller member 150 and the plunger 152 are formed as an integral element. The plunger 152 will be biased against the housing 126, similarly as previously described with the driver 10. A spring 154 may be further used to properly bias the plunger 152 against the housing 126. A cap 156 may be used to allow entry into the housing 126 for assembly purposes.

Still referring to FIG. 8, the cam member 128 is shown with a surface 158, which would correspond to the side surface 58 (or side surface 60) of the driver 10. The surface 158 generally comprises a recessed area 162 formed between sections 166 and 164, which are radially outwardly extending from the cam member 128 with respect to the recessed area 162. That is, the recessed areas 162 form indentations on the cam member 128 compared to the sections 166 and 164. In FIG. 8, the cam member 128 has been rotated, wherein the rolling member 150 is shown buttressed against the respective section 164, thereby providing the desired torque for the driver 10. The interaction between the cam member 128 and the rolling member 150 and the plunger 152 provides the necessary resistant so that the arrangement will set the maximum amount of torque being delivered by the driver 100. Because of the arrangement of the cam assembly and the design of the cam member 128, itself, the driver 100 does not require extra tension or torsion beams or springs to provide the necessary torque delivered by the tool.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A device for delivering a predetermined amount of torque to a tool, said device comprising:
   a handle comprising a housing;
   a cam assembly comprising:
      a cam member located in said housing; and
      a drive shaft integrally formed with said cam member;
   a biasing means disposed between said cam member and said housing, wherein said biasing means is biased against said cam member and is further biased in an opposing direction against said housing, for biasing said cam member against said housing;
   adjustment means for moving said cam member from a first position to a second position, said adjustment means providing torque adjustment means; and
   an adapter for connecting said device to said tool.

2. The device according to claim 1, wherein said biasing means further comprises a pair of plungers located within said housing, said plungers being horizontally spaced from said cam member.

3. The device according to claim 2, wherein said biasing members further comprising a pair of rolling members, each of said rolling members being located between one of said plungers and said cam member.

4. The device according to claim 1, wherein said outer surface of said cam member further comprises a pair of opposing curvilinear side surfaces, said opposing curvilinear surfaces being arranged to interact with said biasing means in both of said first and said second positions to provide predetermined amounts of torque delivery.

5. The device according to claim 1 further comprising a pair of bearings located above and below the cam member.

6. An adjustable device for delivering various predetermined amounts of torque to a tool, said device comprising:
   a handle comprising a housing;
   a cam assembly comprising:
      a cam member located in said housing, said cam member comprising an outer surface; and
      a drive shaft integrally formed with said cam member;
   a biasing means disposed between said cam member and said housing, wherein said biasing means is biased against said cam member and is further biased in an opposing direction against said housing, for biasing said outer surface of said cam member against said housing;
   an adjustment ring connected to said drive shaft, said adjustment ring capable of rotating said drive shaft to a plurality of positions;
   said outer surface of said cam member further comprises a pair of opposing curvilinear side surfaces, said opposing side surfaces being arranged to interact with said biasing means to provide predetermined amounts of torque delivery for each of said plurality of position; and
   means for connecting said device to said tool.

7. The device according to claim 6, wherein said biasing means further comprises a plunger horizontally spaced from said outer surface of one of said curvilinear side surfaces.

8. The device according to claim 7, wherein said biasing means further comprises a rolling member located between said plunger and one of said curvilinear side surfaces.

9. The device according to claim 6, wherein said biasing means, said cam assembly, and said adapter being generally coaxially aligned with one another.

10. The device according to claim 6, wherein said curvilinear side surfaces further comprise:
    a recessed central section; and
    a pair of radially outwardly extending sections contiguous to said recessed central section.

11. The device according to claim 6 further comprising a sleeve connected to said handle and situated over said drive shaft, said sleeve having a plurality of markings, each of said markings indicating one of said predetermined amounts of torque delivery.

12. The device according to claim 6 further comprising a pair of ball bearings located on said top and said bottom surface of said cam member.

13. An adjustable medical device for delivering various predetermined amounts of torque to a tool, said device comprising:
    a handle comprising a housing;
    a cam assembly comprising:
       a cam member located in said housing, said cam member comprising an outer surface; and
       a drive shaft;
    a biasing means disposed between said cam member and said housing, wherein said biasing means is biased against said cam member and is further biased in an opposing direction against said housing, for biasing said cam member against said housing;
    an adjustment ring connected to said drive shaft, said adjustment ring capable of rotating said cam assembly to a plurality of positions;
    said outer surface of said cam member further comprises a pair of opposing curvilinear side surfaces, said side surface being arranged to interact with said biasing means to provide predetermined amounts of torque delivery for each of said plurality of position; and
    means for connecting said device to said tool.

14. The device according to claim 13 further comprising a support sleeve connected to said handle, said support sleeve being located over said drive shaft.

15. The device according to claim 14 further comprising means for indicating predetermined amounts of torque delivery.

16. The device according to claim 15 wherein said indicating means comprises:
   an indicator located on one of said adjustment ring and said support sleeve; and
   and a plurality of markings located on the other of said adjustment ring and said support sleeve, said plurality of markings being capable of being aligned with said indicator, thereby indicating one of said predetermined amount of torques.

17. The device according to claim 13 wherein said biasing means further comprises a pair of plungers located within said housing, said plungers being horizontally spaced from said cam member.

18. The device according to claim 17, wherein said biasing members further comprising a pair of respective rolling members, each of said rolling members being located between one of said plungers and said cam member.

19. The device according to claim 18, wherein said rolling members are integrally formed with said plungers.

20. The device according to claim 13 further comprising a pair of bearings situated at said top and said bottom surfaces of said cam member.

* * * * *